United States Patent
Vandevanter

(10) Patent No.: US 7,485,284 B2
(45) Date of Patent: Feb. 3, 2009

(54) METHOD FOR CHARACTERIZING THE EFFICACY OF AN AGENT TARGETING A PRIMARY CYSTIC FIBROSIS DEFECT

(75) Inventor: Donald R. Vandevanter, Edgewood, WA (US)

(73) Assignee: Novartis Vaccines and Diagnostic, Inc., Emeryville, CA (US)

( * ) Notice: Subject to any disclaimer, the term of this patent is extended or adjusted under 35 U.S.C. 154(b) by 371 days.

(21) Appl. No.: 11/341,954

(22) Filed: Jan. 27, 2006

(65) Prior Publication Data

US 2006/0177375 A1    Aug. 10, 2006

Related U.S. Application Data

(60) Provisional application No. 60/647,477, filed on Jan. 27, 2005.

(51) Int. Cl.
*A61K 49/00*    (2006.01)
(52) U.S. Cl. ........................................................ 424/9.2
(58) Field of Classification Search ........................ None
See application file for complete search history.

(56) References Cited

FOREIGN PATENT DOCUMENTS

| | | |
|---|---|---|
| WO | WO 98/31706 | 7/1998 |
| WO | WO 00/29588 | 5/2000 |
| WO | WO 01/90129 | 11/2001 |

OTHER PUBLICATIONS

Takai et al., "New Therapeutic Key for Cystic Fibrosis: a Role for Lipoxins" *Nature Immunology* 5 (4) :357-358, Apr. 2004.
Lang et al., "Prophylaxis and Therapy of *Pseudomonas aeruginosa* Infection in Cystic Fibrosis and Immunocompromised Patients" *Vaccine* 22 :S44-S48, 2004.
Karp et al., "Defective Lipoxin-Mediated Anti-Inflammatory Activity in the Cystic Fibrosis Airway" *Nature Immunology 5* (4) :388-392, Apr. 2004.

*Primary Examiner*—Jon P Weber
*Assistant Examiner*—Bin Shen
(74) *Attorney, Agent, or Firm*—Morrison & Foerster LLP

(57) ABSTRACT

Generally, the method for characterizing the efficacy of an agent targeting a primary cystic fibrosis defect comprises measuring a change in the status of lung infection in a sample population of subjects administered the agent in comparison to a control sample population of subjects; wherein the subjects in the sample population and the control sample population have the primary cystic fibrosis defect and are uninfected before the agent is administered; wherein a beneficial change in the presence of lung infection in the sample population in comparison to the control sample population is indicative of a treatment effect; and wherein the agent lacks intrinsic antibiotic activity.

23 Claims, 1 Drawing Sheet

METHOD FOR CHARACTERIZING THE EFFICACY OF AN AGENT TARGETING A PRIMARY CYSTIC FIBROSIS DEFECT

CROSS-REFERENCE TO RELATED APPLICATIONS

This application claims priority from U.S. Ser. No. 60/647,477 filed Jan. 27, 2005, the content of which is hereby incorporated by reference herein in its entirety.

TECHNICAL FIELD

The invention relates to methods to demonstrate clinical safety and efficacy of cystic fibrosis therapies. In particular, a method is disclosed for characterizing the efficacy of an agent targeting a cystic fibrosis defect, such as for clinical trial evaluation.

BACKGROUND ART

Cystic fibrosis (CF) is the most common life-shortening genetic disease in Europe and North America. It is caused by inheritance of two mutant alleles of the CFTR (cystic fibrosis transmembrane regulator) gene and results in altered ion transport across epithelial membranes and altered cytokine regulation in the lungs. Persons with CF can experience variable GI disorders that can be managed with nutritional and digestive enzyme supplementation and develop thick mucus in the lungs that impairs mucocilliary transport and impairs the host ability to clear inhaled bacteria. Greater than 90% of deaths in persons with CF in 2003 could be directly or indirectly linked to loss of lung function resulting from cycles of pulmonary obstruction, bacterial infection, and local inflammation (CFF National Patient Registry).

Two commercial therapies have been developed and registered in the US and Europe to combat the thick mucus and chronic bacterial infections that lead to lung function decline in CF: dornase alpha (rhDNase) (Pulmozyme®), and tobramycin inhalation solution (TOBI®). Both products were shown to be effective in persons with CF in prospective, randomized, blinded, placebo controlled clinical studies that compared change in pulmonary function (as $FEV_1\%$ predicted) from baseline relative to placebo. Pivotal efficacy trials for both products were conducted in subjects with moderate to severe lung disease ($FEV_1$ between 25% and 75% of predicted values based on height, age, and sex). Change in pulmonary function is considered a valid surrogate for survival as a clinical study endpoint in CF because of the high incidence of death as a result of loss of lung function in CF, and demonstration that pulmonary function is a strong independent predictor of relative survival for persons with CF. Change in pulmonary function has several significant shortcomings as an endpoint for demonstration of clinical efficacy.

Pulmonary function testing has a high degree of variability, and pulmonary functions of individuals vary sufficiently over time. It is not unusual to observe population standard deviations of 15% to 20% of predicted $FEV_1$. Large standard deviations of measured means require the use of large population samples in order to accurately estimate true mean differences in treatment response between study arms (FIG. 1).

Individuals with CF do not experience uniform rates of pulmonary function loss throughout disease progression, and there can be significant variability in underlying CF disease severity (and thus rate of lung function loss) between individuals. The result is that substantial changes in lung function in individuals during clinical trials can be diluted by modest changes in subjects with less severe disease. The net result of testing "mixed" populations is a reduced observed treatment effect. As observed differences in treatment outcomes decrease between study arms, sample sizes required to prove that observed differences are clinically significant increase (FIG. 1).

Pulmonary function testing requires training and cooperation, and for this reason it is not considered a reliable measure prior to 6 years of age.

Considerable effort has been focused on the development of agents intended to reverse the primary CF defect, thereby providing a "cure" for CF. A variety of approaches are under investigation, including improving the processing of mutant CFTR proteins, providing functional CFTR by gene therapy, and changing the function of alternative epithelial ion channels. Because these therapies are intended to reverse the underlying CF defect, rather than to mitigate downstream biological consequences of the defect, they would ideally be chronic therapies that would be administered before significant disease progression has occurred. This creates a significant challenge for developers of such therapies, in that the current accepted endpoint of change in pulmonary function is employed at the lowest risk and expense after significant disease progression has occurred. Demonstrating the safety and efficacy of a therapy administered before disease progression has occurred would require that a blinded placebo control population develop measurable lung disease. Such a study would require several hundred subjects per arm and duration of years to allow for measurable disease progression.

Nasal potential difference (NPD) is a relatively non-invasive measure that can be collected in infants, but that lacks key features of a viable endpoint for approval. NPD is directly linked to ion movement across the epithelium, and a change in NPD can be used to demonstrate therapeutic mitigation of the CF defect (Konstan et al., *Hum. Gene Ther.* (2004) 15(12): 1255-69). A variation of NPD has recently been proposed in which potential differences are measured in bronchoscopic biopsies of distal airways in young children (Davies et al., *Am. J. Respir Crit. Care Med.*, 176:1015-9 (2005)). Unfortunately, the magnitude to which an individual's potential difference deviates from a normal value does not appear to be particularly predictive of the ultimate severity of their CF lung disease progression (Fajac et al., *Thorax*. (2004) 59(11): 971-6), and there is no algorithm for correlating change in potential difference to change in disease progression.

High-resolution computerized tomography (HRCT) has been proposed as a method to obtain data on lung disease progression in infants and prior to significant disease progression (Marchant et al., *Pediatr. Pulmonol.* (2001) 31(1):24-9; Brody et al., *J. Pediatr.* (2004) 145(1):32-8). HRCT of the lung has the advantages that it can be performed in younger subjects and can identify anatomical events that ultimately lead to loss of pulmonary function, but HRCT does not overcome a basic limitation of lung function as an endpoint: there is substantial variability in the measure, and lung disease does not develop predictably early in the life of an infant with CF. In addition, there is no data set with which a clinician (or regulator) can extrapolate from an early change in HRCT global scoring over time to a risk of CF disease progression or survival, and serial HRCT in infants is not without risk due to cumulative radiation exposure.

Given the challenges with effect on pulmonary function as an efficacy endpoint for regulatory approval of a curative CF therapy, an alternative clinical endpoint more directly related to the primary CF defect is needed. In addition to being measurable in infants with CF, the clinical endpoint ideally also should be methodologically tractable (in that the measure employed is relatively unambiguous and reproducible within and between subjects), statistically robust (where differences in incidence and/or magnitude of the measure between persons with CF and persons without CF can be demonstrated using relatively modest sample sizes), clinically valid (in that clinicians would consider a statistically significant change in the incidence or magnitude of the measure as clinically meaningful with respect to risk of disease progression), and mechanistically sound (in that the measured endpoint can in some way be linked back to the primary defect). The invention addresses these challenges.

The invention takes advantage of previous observations that persons with CF are prone to lung infections with pathogens such as *Pseudomonas aeruginosa, Staphylococcus aureus*, and *Stenotrophomonas maltophilia* at an early age. In 2003, ~50% of persons with CF in the US under age 2 years were reported to have *S. aureus* infections (CFF National Patient Registry), and ~30% were reported to have *P. aeruginosa* infections. It is believed that these opportunistic infections are a result of thickened mucus and loss of mucocilliary transport caused by the primary CF defect.

SUMMARY OF THE INVENTION

The invention relates to a method for characterizing the efficacy of an agent targeting a primary cystic fibrosis defect comprising measuring a change in the presence of lung infection in a sample population of subjects administered the agent in comparison to a control sample population of subjects; wherein the subjects in the sample population and the control sample population have the primary cystic fibrosis defect and are uninfected before the agent is administered; wherein a beneficial change in the presence of lung infection in the sample population in comparison to the control sample population is indicative of a treatment effect; and wherein the agent lacks intrinsic antibiotic activity.

In one aspect, the invention is directed to a method for assaying or characterizing the efficacy of an agent targeting a primary cystic fibrosis defect. In one embodiment, the method comprises measuring the incidence of lung infection in a predetermined period of time in a sample population of subjects administered the agent in comparison to the incidence of lung infection in the predetermined period of time in a control sample population of subjects; and then comparing the incidence of infection in the predetermined period of time in the sample population to the incidence of infection the predetermined period of time in the control sample population; wherein a reduced incidence of infection in the predetermined period of time in the sample population in comparison to the control sample population is indicative of a treatment effect.

In another embodiment, the method comprises calculating a time to first lung infection in a sample population of subjects administered the agent in comparison to a time to first lung infection in a control sample population of subjects; wherein a prolonged time to first infection in the sample population in comparison to the control sample population is indicative of a treatment effect. Using a time such as a median or average time to first infection is preferred. Calculations based on median time are most preferred.

The subjects in the sample population and the control sample population have the primary cystic fibrosis defect. Agents include therapeutic drugs or compositions for treating CF or the symptoms of CF. The subjects' lungs are uninfected before the agent is administered. The agent used in the method should lack intrinsic antibiotic activity, so that such activity will not interfere with the measurement of the incidence of lung infection or the calculation of the time to first lung infection.

The inventive method for characterizing the efficacy of an agent is useful, for example, in evaluating the agent's efficacy in clinical trials, such as one that investigates a treatment for cystic fibrosis.

In a preferred embodiment, the subjects of the sample population and the control population are infants. Preferably, the sample population, preferably of infants, are characterized by a lack of disease progression. Lack of disease progression means before presentation of chronic respiratory symptoms or before detection of airway abnormalities. Airway abnormalities may be determined by high resolution computerized tomography and include air trapping and/or airway wall thickening. Thus, the preferred patient population are infants without chronic respiratory symptoms and/or without airway abnormalities such as air trapping or airway wall thickening. In one embodiment, an asymptomatic subject is indicative a of CF patient who has not shown disease progression.

Preferably, the control sample population is administered a placebo.

In another preferred embodiment, the treatment effect due to the reduced incidence of infection in the predetermined period or the prolonged median time to first infection is a significant treatment effect, which can be measured, for example, using a two-tailed Fisher's Exact test with alpha=0.05.

In one embodiment, the lung infection of the method may be caused by at least one pathogen selected from the group consisting of Pseudomonas, Staphylococcus and Stenotrophomonas, such as *Pseudomonas aeruginosa, Staphylococcus aureus*, or *Stenotrophomonas maltophilia*.

In a preferred embodiment, the presence of infection or the incidence of infection is measured by an in vitro culture of bacteria or by quantitation of host antibodies directed against bacteria, for example, measured using a fluid obtained from a subject such as mucus or serum.

DETAILED DESCRIPTION OF THE INVENTION

Figure 1:
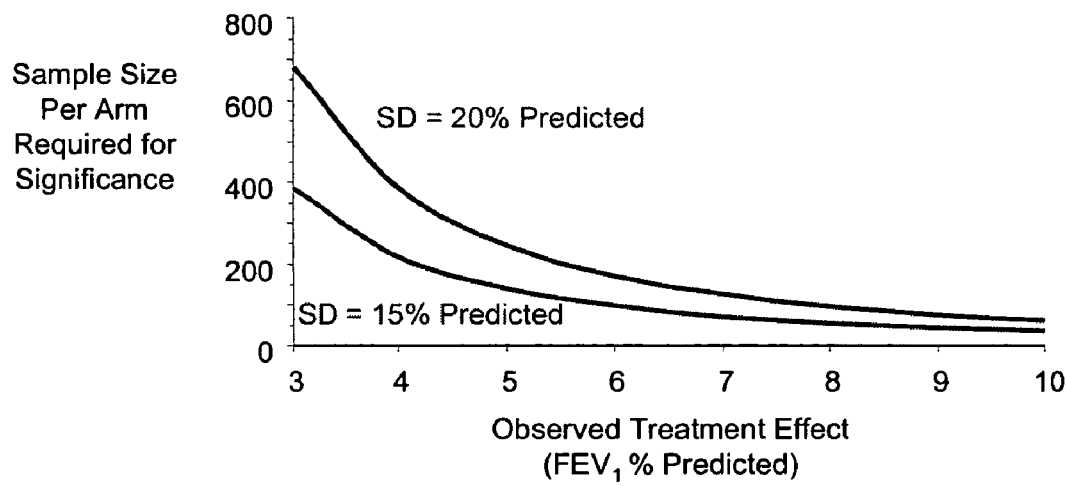
FIG. 1 shows the effects of standard deviation and observed treatment effect on clinical trial design.

In one aspect, the invention relates to measuring a change in the presence of lung infection in a single population of subjects administered the agent in comparison to a control sample. A "change" in the presence of lung infection may relate to any measurable change which is related to the presence or absence of lung infection. For example, a change may be measured by measuring the incidence of lung infection in a pre-determined period of time in a sample versus control population. In another aspect, a change in the presence of lung infection may include calculating the time to first lung infection in a sample versus a control sample.

A "beneficial change" in the status of lung infection primarily relates to any measurable reduction in the sample population of subjects of the status of lung infection with respect to the control sample population. The status of lung infection refers to the relative state of the lung infection. For example, the status may refer to the presence or absence of lung infection. A beneficial change of status may include, for example, a reduced incidence of infection in a pre-determined period of time in a sample population in comparison to the control population or a prolonged time to first infection or in the sample population in comparison to the control sample population. Such a beneficial change is indicative of a treatment effect. Prolonged time may be, but is not limited to, prolonged actual time, median time or average time. Preferably, median time is measured.

A method for characterizing the efficacy of an agent targeting the primary CF defect and lacking intrinsic antibiotic activity is proposed in which clinical studies employ the hypothesis that clinically significant reversal of the primary CF defect results in a reduced incidence of opportunistic infections in uninfected infants with CF. Incidence of infection or the presence of infection can be measured by any number of validated, predetermined methods, including (but not limited to) in vitro culture of oropharyngeal swab samples, in vitro culture of bronchoalveolar lavage fluids, or quantitation of host antibodies in subject serum directed at bacterial haptens such as exotoxin A, elastase, or lipopolysaccharides (Burns et al., *J. Infect. Dis.* (2001) 183(3):444-52; West et al., *JAMA* (2002) 287(22):2958-67).

Infants with CF are prone to opportunistic respiratory tract infection with pathogens including *Staphylococcus aureus*, *Pseudomonas aeruginosa*, and *Stenotrophomonas maltophilia* at dramatically higher incidences than the general population, with cross-sectional incidences ranging from 20% to 50% (depending on pathogen) in infants with CF in the US less than 2 years of age. (Cystic Fibrosis Foundation, National Patient Registry Annual Data Report (2003) Bethesda, Md. ("CFF National Patient Registry")). Longitudinal analyses of infant cohorts have demonstrated respiratory tract infection with *P. aeruginosa* of about 50% (depending on assay) by age 2 years (West et al., supra) and 70% (West et al., supra) to greater than 95% (Burns et al., supra) by age 3 years. Respiratory tract *P. aeruginosa* infection in infants is a strong predictor of subsequent progression of pulmonary disease (Demko et al., *J. Clin. Epidemiol.* (1995) 48:1041-1049; West et al., *supra*; Li et al., *JAMA* (2005) 293(5):581-8). Because loss of lung function is the primary cause of mortality in CF (CFF National Patient Registry, supra), a clinical trial endpoint in which a change in lung physiology resulting in reduced incidence of infection should prove clinically meaningful to physicians, provided that the test agent has no intrinsic antibiotic activity.

Because the incidence of respiratory tract infection in infants with CF is fairly high, a statistically significant treatment effect can be demonstrated with reasonably modest sample sizes. Sample sizes required to assure 90% power for studies seeking a 50% treatment effect (i.e. in which the incidence of infection is reduced 50% over a given period by treatment) are provided as a function of control arm infection incidence in Table 1.

TABLE 1

Sample Sizes Required for 90% Statistical Power as a Function of Infection Incidence

| Control Infection Incidence | 40% | 30% | 20% | 10% |
|---|---|---|---|---|
| Treatment Infection Incidence | 20% | 15% | 10% | 5% |
| Treatment Effect Odds ratio | 0.375 | 0.412 | 0.444 | 0.474 |
| Sample Size Required per Arm* | 98 | 144 | 237 | 513 |

*alpha = 0.05; one-sided two-group continuity-corrected $\chi^2$ test of equal proportions For instance, the sample size required to obtain 90% power for a two-armed study intended to show that a treatment-related reduction of infection incidence from 30% to 15% was significant at p=0.05 would be 144 subjects per arm.

Perhaps the most important attribute of a first infection clinical trial endpoint for regulatory approval is that a trial would be conducted in the very population for which a "cure" is intended. Advantageously, a database of safety and efficacy in infants with CF may be developed under strictly controlled and monitored clinical trial conditions rather than to rely on post-marketing extrapolation of treatment benefits derived in older, sicker subjects back to infants.

Commercial considerations also favor development of a CF cure in infants. For instance, the market size for a CF drug approved for the treatment of asymptomatic patients is substantially larger than one approved for the treatment of patients with moderate to severe lung disease. This is because drug manufacturers can be confident that a CF drug shown to be safe and effective in relatively healthy subjects will also be considered for treatment of patients with more advanced CF disease, and that extrapolation of benefit into that population is much more likely to occur than the converse.

There is no precedent for regulatory approval of a CF cure, and the path used for the previous approvals of rhDNase and TIS does not appear to be commercially viable. Reduction in time to infection appears to be a scientifically valid and commercially viable efficacy endpoint for regulatory approval of a CF cure. Preferably, clinical/scientific consensus as to which assay(s) to standardize to detect respiratory tract infection (e.g. Burns et al., *supra*; West et al., *supra* ) will be necessary, and normative pediatric data measured by the chosen assay must be collected in order to further validate the endpoint and allow adequate powering of pivotal trials.

The invention has distinct advantages over current clinical endpoints:
1) Clinical testing can be performed in the ultimate target population for the drug candidate, infants with CF. This will allow a much more direct evaluation of clinical efficacy as a "cure" for CF, and will facilitate product commercialization.
2) Because the incidence of bacterial lung infections in CF infants is relatively high, and because the test of efficacy does not require the comparison of population means for a continuous measure (such as pulmonary function), sample sizes required to demonstrate efficacy are reduced.

The sample population or the control sample population that comprise infants are preferably less than six years old, more preferably less than three years old, and most preferably less than two years old. Infants that are younger than two years old represent a high risk group and thus are preferred subjects for the inventive method.

In one aspect, the method comprises measuring the incidence of lung infection in a predetermined period of time. The optimum time depends on the underlying incidence in a control population. Preferably, the predetermined period of time is six months, which is the minimum time required by the FDA for registration of the agent for chronic conditions, for example, in Phase III trials. Shorter predetermined periods of time may be used, such as three months, for Phase II trials, which may show proof of concept. Longer durations of time, such as a year or more, may be necessary if the incidence of lung infection is reduced in certain populations.

In another aspect, the median time to first lung infection is calculated. Essentially, this calculation will show a rate at which infection develops in a population, and thus may be considered a survival analysis.

A detailed description of the invention having been provided above, the following examples are given for the purpose of illustrating the invention and shall not be construed as being a limitation on the scope of the invention or claims.

EXAMPLE 1

Figure 2:
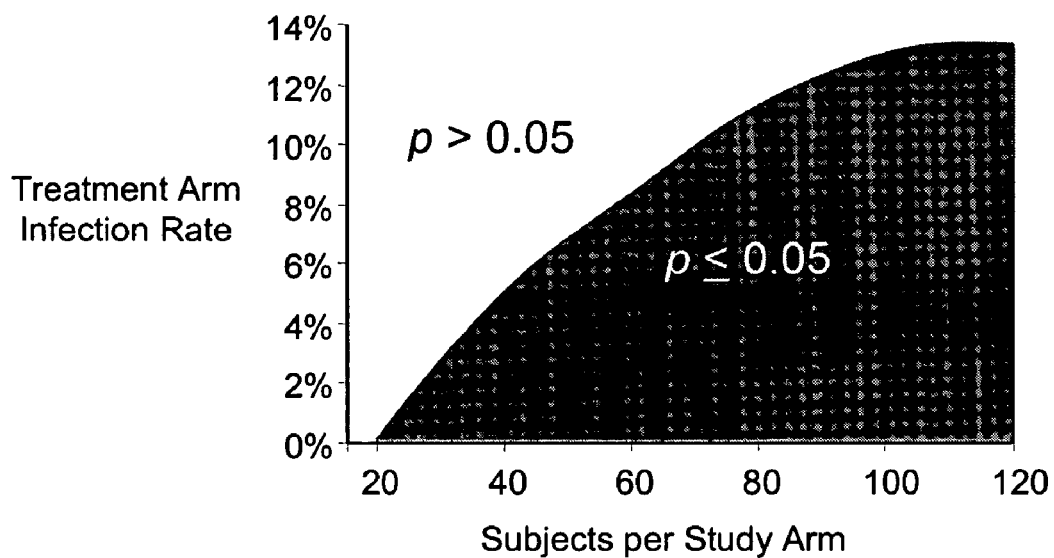
FIG. 2 shows the effect of sample size on significance of treatment outcome in a 1:1 randomized study with an incidence of 25% infection in the placebo arm.

A study is proposed in which 200 subjects are randomized in a 1:1 prospective manner, balancing for known risk factors such as pancreatic insufficiency, BMI, and history of CF complications such as muconeum ilieus. To be included in the study, subjects must be less than two years of age, have a clinical diagnosis of CF (e.g. pilocarpine sweat test), without evidence of bacterial infection at screening, and informed consent from legal guardian. Subjects are administered either placebo or active therapy according to schedule for a predetermined period of time (e.g. 6 months) predicted to result in a 25% incidence of bacterial infection in the population. Both subjects and investigators are blinded to the identity of treatments. At intervals throughout the study, subjects are assessed for the presence of bacterial infection using a previously validated assay technique. At study termination, the incidence of bacterial infection in the placebo group is compared to the incidence of infection in the treatment arm. Significance in difference is testing using a two-tailed Fisher's Exact test with alpha=0.05. If an incidence of 25% infection (i.e. 25/100 subjects) is observed in the placebo arm, any incidence of infection below 13% 13/100 subjects) in the treatment arm represents a significant treatment effect (FIG. 2).

EXAMPLE 2

A study design comparable to that in Example 1 is employed, except that the duration of treatment exposure is significantly shortened, with an expected 10% net incidence of infection in a comparable untreated population over the study period. A total of 300 subjects are treated per arm and assessed for bacterial infection at termination. If a 10% (30/300) incidence of infection is observed in the placebo arm, any incidence of infection in the treatment arm below 5.7% (17/300 subjects) represents a statistically significant therapeutic effect (Table 2).

TABLE 2

SIGNIFICANCE OF TREATMENT EFFECT AS A FUNCTION OF EVENT INCIDENCE IN A 600 SUBJECT STUDY

| N = 300 placebo events | per arm placebo incidence | treatment events | treatment incidence | p |
|---|---|---|---|---|
| 30 | 10.0% | 10 | 3.3% | 0.001562 |
| 30 | 10.0% | 11 | 3.7% | 0.00314 |
| 30 | 10.0% | 12 | 4.0% | 0.005927 |
| 30 | 10.0% | 13 | 4.3% | 0.010575 |
| 30 | 10.0% | 14 | 4.7% | 0.01793 |
| 30 | 10.0% | 15 | 5.0% | 0.029029 |
| 30 | 10.0% | 16 | 5.3% | 0.045058 |
| 30 | 10.0% | 17 | 5.7% | 0.067293 |

The invention claimed is:

1. A method for characterizing the efficacy of an agent targeting a primary cystic fibrosis defect comprising
measuring a change in the status of lung bacterial infection in a sample population of subjects administered the agent in comparison to a control sample population of subjects;
wherein the subjects in the sample population and the control sample population have the primary cystic fibrosis defect and are uninfected before the agent is administered;
wherein a beneficial change in the status of the lung bacterial infection in the sample population in comparison to the control sample population is indicative of a treatment effect; and
wherein the agent lacks intrinsic antibiotic activity.

2. The method of claim 1 wherein the measuring step further comprises
a) measuring the incidence of lung bacterial infection in a predetermined period of time in the sample population of subjects administered the agent in comparison to the incidence of lung bacterial infection in the predetermined period of time in the control sample population of subjects; and
b) comparing the incidence of bacterial infection in the predetermined period of time in the sample population to the incidence of infection the predetermined period of time in the control sample population;
wherein the beneficial change is a reduced incidence of bacterial infection in the predetermined period of time in the sample population in comparison to the control sample population.

3. The method of claim 1 wherein the measuring step further comprises:
calculating the time to first lung bacterial infection in the sample population of subjects administered the agent in comparison to the time to first lung bacterial infection in the control sample population of subjects;
wherein the beneficial change is a prolonged time to first bacterial infection in the sample population in comparison to the control sample population.

4. The method of claim 2 wherein the incidence of bacterial infection in the lung of a subject is measured by an in vitro culture of bacteria or by quantitation of host antibodies directed against bacteria.

5. The method as in claim 3, wherein the time to first bacterial infection is a median time.

6. The method of claim 2 wherein the subjects of the sample population and the control population are infants.

7. The method of claim 3 wherein the subjects of the sample population and the control population are infants.

8. The method of claim 2 wherein the lung bacterial infection is caused by at least one pathogen selected from the group consisting of *Pseudomonas, Staphylococcus* and *Stenotrophomonas*.

9. The method of claim 3 wherein the lung bacterial infection is caused by at least one pathogen selected from the group consisting of *Pseudomonas, Staphylococcus* and *Stenotrophomonas*.

10. The method as in claim 8 wherein the pathogen is *Pseudomonas aeruginosa, Staphylococcus aureus*, or *Stenotrophomonas maltophilia*.

11. The method as in claim 9 wherein the pathogen is *Pseudomonas aeruginosa, Staphylococcus aureus*, or *Stenotrophomonas maltophilia*.

12. The method of claim 2 wherein the treatment effect is a significant treatment effect.

13. The method of claim 3 wherein the treatment effect is a significant treatment effect.

14. The method of claim 12 wherein the significant treatment effect is determined using a two-tailed Fisher's Exact test with alpha=0.05.

15. The method of claim 13 wherein the significant treatment effect is determined using a two-tailed Fisher's Exact test with alpha=0.05.

16. The method of claim 2 wherein the method evaluates efficacy of the agent in a clinical trial.

17. The method of claim 3 wherein the method evaluates efficacy of the agent in a clinical trial.

18. The method of claim 16 wherein the clinical trial investigates a treatment for cystic fibrosis.

19. The method of claim 17 wherein the clinical trial investigates a treatment for cystic fibrosis.

20. The method of claim 2 wherein the control sample population is administered a placebo.

21. The method of claim 3 wherein the control sample population is administered a placebo.

22. The method of claim 2 wherein the uninfected subjects lack disease progression before the measuring step.

23. The method of claim 3 wherein the uninfected subjects lack disease progression before the measuring step.

* * * * *